US012789002B2

(12) United States Patent
Phillips

(10) Patent No.: US 12,789,002 B2
(45) Date of Patent: Nov. 10, 2026

(54) MAGNETIC STIMULATION APPARATUS, METHOD, AND SYSTEM

(71) Applicant: Wave Neuroscience, Inc., Newport Beach, CA (US)

(72) Inventor: James William Phillips, Fountain Valley, CA (US)

(73) Assignee: Wave Neuroscience, Inc.

( * ) Notice: Subject to any disclaimer, the term of this patent is extended or adjusted under 35 U.S.C. 154(b) by 1213 days.

(21) Appl. No.: 17/453,479

(22) Filed: Nov. 3, 2021

(65) Prior Publication Data

US 2022/0134123 A1 May 5, 2022

Related U.S. Application Data

(60) Provisional application No. 63/109,337, filed on Nov. 3, 2020.

(51) Int. Cl.

*A61N 2/12* (2006.01)
*A61N 2/00* (2006.01)
*A61N 2/02* (2006.01)
*A61N 2/06* (2006.01)

(52) U.S. Cl.

CPC ............... *A61N 2/12* (2013.01); *A61N 2/004* (2013.01); *A61N 2/02* (2013.01); *A61N 2/06* (2013.01)

(58) Field of Classification Search

CPC . A61N 2/12; A61N 2/004; A61N 2/02; A61N 2/06
USPC ........................................................ 600/9–15
See application file for complete search history.

(56) References Cited

U.S. PATENT DOCUMENTS

| | | | | |
|---|---|---|---|---|
| 3,879,622 | A | 4/1975 | Ecklin | |
| 4,267,647 | A | 5/1981 | Anderson, Jr. et al. | |
| 2008/0296987 | A1 | 12/2008 | Jang et al. | |
| 2011/0034822 | A1* | 2/2011 | Phillips | A61B 5/4082 600/9 |
| 2011/0112427 | A1* | 5/2011 | Phillips | A61B 5/407 600/9 |
| 2015/0025297 | A1* | 1/2015 | Pan | A61N 2/006 600/13 |
| 2016/0193476 | A1* | 7/2016 | Helekar | A61N 2/12 600/15 |
| 2016/0331990 | A1* | 11/2016 | Mohamed | A61N 2/12 |

(Continued)

FOREIGN PATENT DOCUMENTS

| | | | | |
|---|---|---|---|---|
| WO | WO-2010129997 | A1 * | 11/2010 | A61N 1/06 |
| WO | WO-2016116747 | A1 * | 7/2016 | A61N 2/02 |
| WO | 2022099269 | A1 | 5/2022 | |

*Primary Examiner* — Sunita Reddy
(74) *Attorney, Agent, or Firm* — K&L Gates LLP; Brian J. Novak; Hal Gibson

(57) ABSTRACT

An apparatus and method configured to generate a magnetic field applied to a target location. The apparatus and method include a magnetic stimulation apparatus, including a permanent magnet configured to generate a magnetic field, and a magnetic shield configured to shield at least one target region from the magnetic field generated by the permanent magnet, wherein the magnetic shield includes at least one gap region configured to expose at least one other target region to the magnetic field generated by the permanent magnet. At least one gap region is moveable so that the shielded at least one target region is exposed to the magnetic field at the other target region.

20 Claims, 5 Drawing Sheets

(56) References Cited

U.S. PATENT DOCUMENTS

| | | | | |
|---|---|---|---|---|
| 2018/0214710 | A1* | 8/2018 | Charles .................. | A61B 5/369 |
| 2019/0209855 | A1* | 7/2019 | Helekar ................. | A61B 5/369 |

* cited by examiner

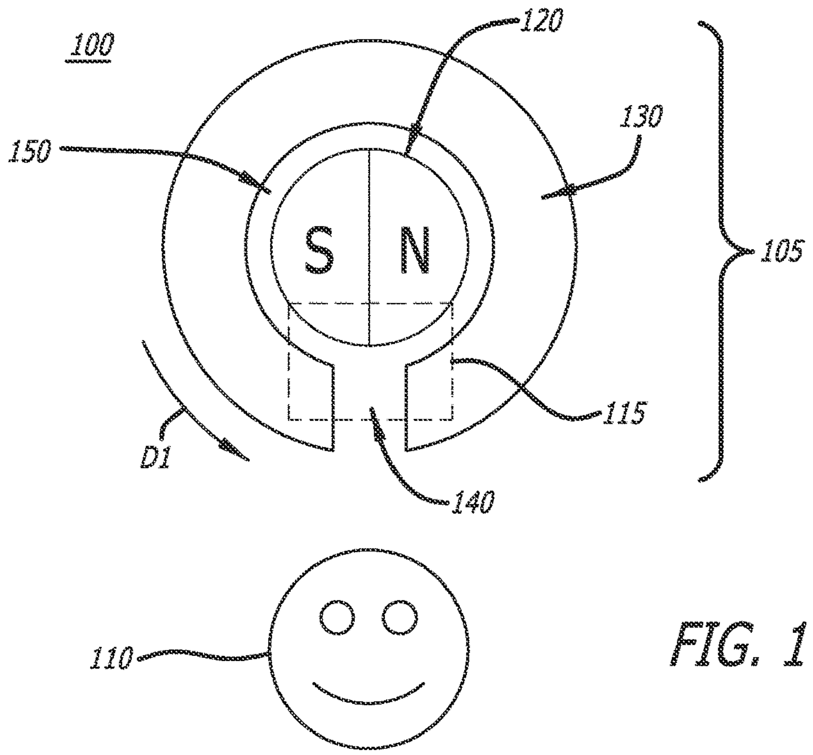
FIG. 1
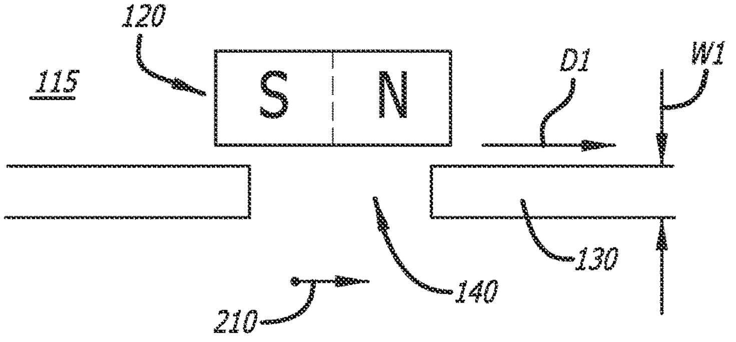
FIG. 2A
FIG. 2B
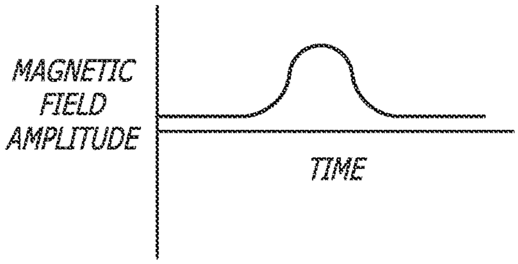
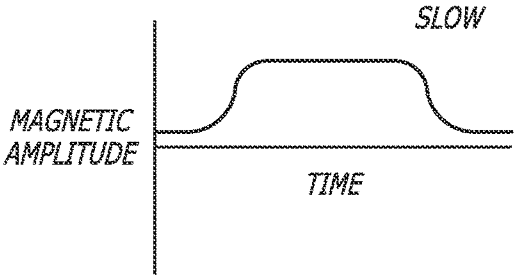
FIG. 2C

MAGNETIC STIMULATION APPARATUS, METHOD, AND SYSTEM

PRIORITY

This application claims priority to U.S. Provisional Application No. 63/109,337, filed Nov. 3, 2020, which is incorporated by reference in its entirety into this application.

BACKGROUND

Over the years, magnetic field treatment has grown in popularity as a method of treating physical and mental disorders. As popularity for this type of treatment grows, it has shown that applying alternating magnetic fields at specific frequencies upon a user produced therapeutic and advantageous effects.

Currently, alternating magnetic field treatments such as Repetitive Transcranial Magnetic Stimulation (rTMS) use an electromagnet that generates a series of alternating magnetic field pulses. However, when generating low frequency magnetic field pulses using an electromagnet such as in rTMS, high current is required which generates a significant amount of heat. Additionally, the alternating magnetic field pulses are not easily directed to a particular location, and involve a large and expensive device to generate the high current pulse to the coil.

To address this, techniques such as moving permanent magnets are used to generate an alternating magnetic field. The use of permanent magnets, however, causes the magnets and their magnetic fields to create a push-pull effect on each other which limits performance. As such, there is a need for increased spacing to avoid this effect and the consequential excessive wear on motors, gears, and belts.

SUMMARY OF THE INVENTION

The present disclosure relates to magnetic field treatment technology. Specifically, to magnetic stimulation including a permanent magnet and movable magnetic shielding.

The various embodiments of the present magnetic stimulation apparatus and method have several features, no single one of which is solely responsible for the desirable attributes provided herein. Without limiting the scope of the present embodiments as expressed by the claims that follow, the more prominent features will be discussed briefly. After considering this discussion, and particularly after reading the section entitled "Detailed Description," one will understand how the magnetic stimulation apparatus and method of the present embodiments can be used in various combinations to provide the advantages described herein.

In an exemplary embodiment, a magnetic stimulation apparatus includes a permanent magnet configured to generate a magnetic field, and a magnetic shield configured to shield at least a first target region from the magnetic field generated by the permanent magnet, wherein the magnetic shield includes at least one gap region configured to expose a second target region to the magnetic field generated by the permanent magnet. At least one gap region may be moveable. In an exemplary embodiment, the gap region is moveable so that the first target region originally shielded by the magnetic shield is exposed and becomes the second target area exposed to the magnetic field after movement of the magnetic shield. In an exemplary embodiment, at least one gap region is moveable at a predetermined speed.

In an exemplary embodiment, a magnetic stimulation method includes generating a magnetic field by a permanent magnet, and shielding, by a magnetic shield, at least one target region from the magnetic field generated by the permanent magnet, wherein the magnetic shield includes at least one gap region configured to expose a specific target region to the magnetic field generated by the permanent magnet. The at least one gap region may be moveable. The one gap region may be movable at a predetermined frequency. The one gap region may be moveable at a constant frequency, a set frequency, a variable frequency, or combinations thereof.

BRIEF DESCRIPTION OF THE DRAWINGS

FIG. 1 is an exemplary representative view of a magnetic stimulation system according to an exemplary embodiment of the present disclosure.

FIG. 2A is an exemplary partial representative view of the magnetic stimulation device according to an exemplary concept of the present disclosure.

FIGS. 2B and 2C show a graph of an exemplary magnetic field according to an exemplary embodiment of the present disclosure as shown in FIG. 2A.

DETAILED DESCRIPTION OF THE EMBODIMENTS

Figure 3A:
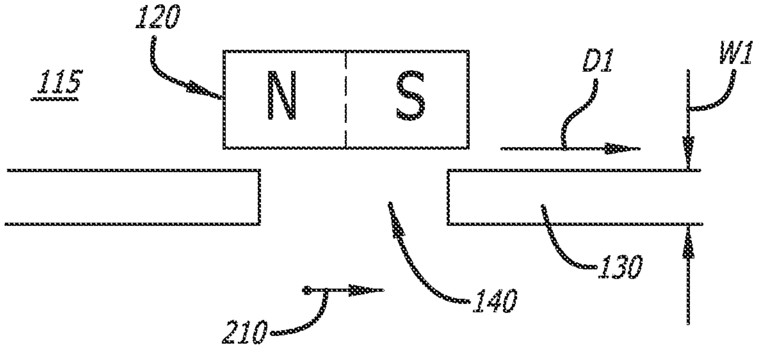
FIG. 3A is a partial representative component sectional representative detail view of the magnetic stimulation device according to an exemplary embodiment of the present disclosure.

Example devices, methods, and systems are described herein. Any example embodiment or feature described herein is not necessarily to be construed as preferred or advantageous over other embodiments or features. The example embodiments described herein are not meant to be limiting. It will be readily understood that certain aspects of the disclosed devices, systems, and methods can be arranged and combined in a wide variety of different configurations, all of which are contemplated herein. Accordingly, any feature, component, concept, or function may be duplicated, removed, combined, or otherwise used alone or in combination with any other combination of other features, components, concepts, or functions described herein or otherwise known to a person of skill in the art.

The particular arrangements shown in the figures should not be viewed as limiting. It should be understood that other embodiments might include more or less of each element shown in a given figure. Further, some of the illustrated elements may be combined or omitted. Yet further, an example embodiment may include elements that are not illustrated in the figures.

The present disclosure provides a device for pulsed magnetic field stimulation. The device may be incorporated into a helmet, with multiple magnets and shields incorporated to provide magnetic field stimulation pulses to many areas of a user, such as, but not limited to, the brain of the user. The device can be incorporated as, but is not limited to, a handheld device that a user could place next to their scalp or other body region whenever stimulation is required. The handheld device may include an elongated device, such as a pen-shape. Additionally, the device could be set into a headrest or into a backrest in order to apply magnetic field stimulation to other body regions, such as, but not limited to, the head, foot, and/or back. The device may be incorporated into the shape of a headset or other feature for positioning on the head of a user. For example, the device may comprise of a helmet or harness configured to attach to the user's head, in which the helmet may support and/or enclose the components of the magnets and/or shielding as described herein.

Because there is a need to generate an alternating magnetic field using permanent magnets that do not require moving the magnets, exemplary embodiments of the present disclosure provide for a moveable magnetic shield that alternately exposes or shields a permanent magnet from a target region. The permanent magnet may be stationary and/or moveable.

FIG. 1 depicts a magnetic stimulation system 100 according to an exemplary embodiment of the present disclosure. The magnetic stimulation system 100 includes, but is not limited to, a user 110 and a magnetic stimulation device 105.

In an exemplary embodiment, the user 110 can be, but is not limited to, a human user. The user may be a mammal, animal, human, or other organic, living object. The user 110 would be the recipient of a magnetic field applied by the magnetic stimulation device 105 to a specific region requiring magnetic stimulation. In an exemplary embodiment of the present disclosure, the magnetic stimulation device 105 is positioned over a target region of the user 110. In an exemplary embodiment, the magnetic stimulation device 105 is a wearable worn by the user 110.

In an exemplary embodiment, the magnetic stimulation device 105 includes, but is not limited to, a permanent magnet 120, a magnetic shield 130, and a non-shielded region 140. There may be a gap 150 between the permanent magnet 120 and the magnetic shield 130.

In an exemplary embodiment of the present disclosure, the permanent magnet 120 creates its own persistent magnetic field and can be, but is not limited to, neodymium iron boron (DnFeB), which has an energy product range up to 50 MGOe (Mega Gauss Oersted), samarium cobalt (SmCo), with an energy product range of up to 30 MGO3, alnico, ceramic, and/or ferrite. The polarity of the magnetic field may be set based on the orientation of the permanent magnet 120 in regard to a target region of the user 110 and/or an orientation of the housing or device for coupling the magnetic stimulation device to the user.

The permanent magnet 120 can be any shape allowing the magnetic shield 130 to be positioned between at least one outer wall of the permanent magnet 120 and the user 110 at any given time. In an exemplary embodiment, the permanent magnet 120 is cylindrical in shape and the magnetic shield 130 is rotatable about the outer diameter of the permanent magnet 120. In another embodiment, the permanent magnet is disk-shaped.

Moreover, the permanent magnet 120 can be diametrically magnetized or axially magnetized based on intended use and type of treatment administered to user 110. In the exemplary embodiment, the permanent magnet 120 is diametrically magnetized. Although a permanent magnet is shown and described herein, other magnetic sources, such as a wire coil configured to pass current there through is also contemplated and understood to be within the scope of the instant disclosure for use as a magnetic source.

In an exemplary embodiment, the permanent magnet 120 is moveable in relation to the magnetic shield 130. In this embodiment, movement of the permanent magnet 120 is calculated based on the movement of the magnetic shield 130. Also described herein in terms of the permanent magnet (or magnetic source) being moveable, the movement is understood to be relative. Therefore, in an exemplary embodiment the shielding may be configured to remain stationary relative to the patient, and/or the housing of the device, while the magnetic source may be moved relative to the shielding. Alternatively, the magnetic source may be configured to remain stationary relative to the patient, and/or the housing of the device, while the shielding may be moved relative to the magnetic source. Alternatively, both the magnetic source and the shielding may be configured to move relative to the housing and to each other.

In an embodiment of the present disclosure, the magnetic shield 130 is a material with a relatively high permeability in response to an applied magnetic field. The magnetic shield 130 can be, but is not limited to, Mu-metal® and/or another alloy with very high permeability. Moreover, the shape of the magnetic shield 130 is any that allows a gap 150 to be formed between an outer wall of the permanent magnet 120 and an inner wall of the magnetic shield 130.

In the first exemplary embodiment, the shape of magnetic shield 130 is a cylinder surrounding the permanent magnet 120. The magnetic shield 130 may have an internal dimension greater than the external dimension of the permanent magnet 120 so that a gap 150 is created in between the permanent magnet and magnetic shield of the shielded region. Moreover, in the first exemplary embodiment of the present disclosure, the magnetic shield 130 may be moved between the permanent magnet 120 and the target region of the user 110 exposing the permanent magnet through a non-shielded region 140 of the magnetic shield 130. This occurs in region 115 which will be shown and discussed, as embodiments, in greater detail below.

In an embodiment of the present disclosure, the non-shielded region 140 is a region of the magnetic shield 130 situated between an outer wall of the permanent magnet 120 and the user 110 that exposes the permanent magnet 120 and increases magnetic field exposure of the user 110 to the magnetic field produced by the permanent magnet 120. In an embodiment of the present disclosure, the non-shielded region 140 is rotatable about the permanent magnet 120 and allows the permanent magnet 120 to apply a magnetic pulse to the user 110 via the non-shielded region 140.

In the first exemplary embodiment of the present disclosure, the magnetic shield 130 has at least one non-shielded region 140, and the magnetic shield 130 is moved in a specific direction at a specific speed allowing the non-shielded region 140 to pass adjacent to the user 110 at a specific interval to create a magnetic pulse. If the non-shielded region 140 is relatively large, then a magnetic pulse applied to the user 110 will be of longer duration and will begin to resemble a rectangular pulse.

The magnetic shield 130 may rotate in a one or more directions. The magnetic shield 130 may rotate for full and/or partial rotations. The magnetic shield 130 may rotate at a set frequency, speed, oscillation, or combination thereof. The magnetic shield 130 may rotate at a variable frequency, speed, oscillation, or combination thereof. In an exemplary embodiment, the magnetic shield 130 may rotate in full continuous and sequential rotations in the same direction at a constant angular velocity. In an exemplary embodiment, the magnetic shield 130 may oscillate between opposing directions through partial rotations. In an exemplary embodiment, the non-shielded region 140 remains generally directed toward the patient or orthogonal to the surface of the patient's head. The non-shielded region 140 may therefore not be directed away from the patient's head to provide magnetic stimulation away from the patient and into the environment. Such arrangement may minimize the unintended exposure of magnetic stimulation to others administering treatment to a patient.

The alternating magnetic field produced by the magnetic stimulation device 105 creates an alternating magnetic field applied to the user 110. The characteristics of the magnetic field are affected by, but not limited to, the type of permanent magnet 120 used (or other magnetic source), the orientation of the permanent magnet 120 (or other magnetic source), the distance of the permanent magnet 120 from the user 110, the amount of magnetic shield 130 provided, the amount of time the permanent magnet is un-shielded and the duty cycle of a non-shielded region 140.

FIG. 2A is a partial component detail view representing the magnetic stimulation system 100 according to an exemplary embodiment of the present disclosure. More specifically, the region 115 which includes, but is not limited to, a permanent magnet 120 with north and south poles positioned tangential to a target region 210 (shown as a vector) of a user 110 and the magnetic shield 130 with thickness width W1. In an exemplary embodiment, a thick magnetic shield is considered as being sufficiently thick such that a magnetic field amplitude through the shielded portion of the magnetic shield is approximately half or less than the non-shielded magnetic field amplitude of the magnet. Other exemplary thicknesses are provided herein and described with respect to other embodiments. Exemplary thicknesses of the magnetic shield may be sufficiently thick in which approximately or less than 25% of the magnetic field amplitude is shielded, approximately or less than 25% of the magnetic field amplitude is shielded, approximately or less than 50% of the magnetic field amplitude is shielded, approximately or more than 50% of the magnetic field amplitude is shielded, approximately or more than 75% of the magnetic field amplitude is shielded, approximately or more than 90% of the magnetic field amplitude is shielded, or substantially all of the magnetic field amplitude is shielded.

Here, when the magnetic shield 130 is moved in the direction D1 such that the non-shielded region 140 moves tangentially to the permanent magnet 120 and is situated between the permanent magnet 120 and target region 210, a unipolar changing magnetic field is created during the time the non-shielded region 140 allows the magnetic field generated by the permanent magnet 120 to penetrate the target region 210.

FIG. 2B shows a graph of magnetic field applied to the target region 210 over time when the magnetic shield 130 is moved relatively quickly in direction D1 according to the exemplary embodiment of the present disclosure as shown in FIG. 2A.

In the graph, the x-axis is time and the y-axis shows magnetic field amplitude of the magnetic field applied to the target region 210 by the permanent magnet 120 in the configuration shown in FIG. 2A. In this embodiment, the magnetic field pulse is short in duration due to the duty cycle of the moving magnetic shield 130. In an exemplary embodiment, similar results as shown in FIG. 2A can be achieved by decreasing the size of non-shielded region 140.

FIG. 2C shows a graph of magnetic field applied to the target region 210 over time when magnetic shield 130 is moved relatively slow in direction D1 according to the first embodiment of the present disclosure as shown in FIG. 2A.

In the graph, the x-axis is time and the y-axis shows magnetic field amplitude of the magnetic field applied to the target region 210 by the permanent magnet 120 in the configuration shown in FIG. 2A. In this embodiment, the magnetic field pulse applied to target region 210 is long in duration due to the duty cycle of the moving magnetic shield 130 and may resemble a rectangular pulse waveform. In an exemplary embodiment, similar results as shown in FIG. 2C can be achieved by increasing the size of non-shielded region 140.

FIG. 3A is an exemplary partial component representative detail view of the magnetic stimulation system 100 according to an exemplary embodiment of the present disclosure. This embodiment shares similar elements as those described above, as such their descriptions will be omitted and only differences will be described herein.

Here, the permanent magnet 120 is positioned similarly as FIG. 2A but with an orientation in the opposite direction as shown in FIG. 2A. As such, when the magnetic shield is moved in the direction D1 and the non-shielded region 140 moves between the permanent magnet 120 and target region 210, a magnetic field is generated with opposite polarity as produced in FIG. 2A.

Figure 3B:
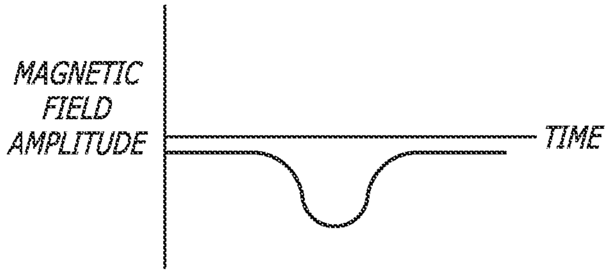
FIG. 3B shows a graph of an exemplary magnetic field according to an exemplary embodiment of the present disclosure as shown in FIG. 3A.

FIG. 3B shows a graph of magnetic field applied to the target region 210 over time according to the exemplary embodiment of the present disclosure as shown in FIG. 3A. In the graph, the x-axis is time and the y-axis shows magnetic field amplitude of the magnetic field applied to the target region 210 by the permanent magnet 120 in the configuration shown in FIG. 3A.

Figure 4A:
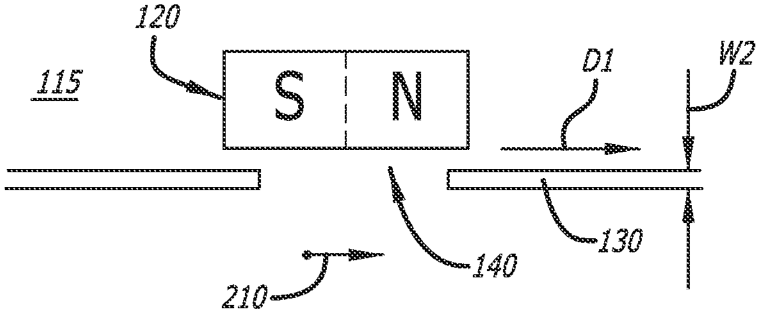
FIG. 4A is an exemplary partial component sectional representative detail view of the magnetic stimulation device according to an exemplary embodiment of the present disclosure.

FIG. 4A is a partial component representative detail view of the magnetic stimulation system 100 according to an exemplary embodiment of the present disclosure. This embodiment shares similar elements as those described above, as such their descriptions will be omitted and only differences will be described herein.

Here, the magnetic shield 130 moves in the direction D1 and is relatively thin with thickness width W2 of the magnetic shield 130 being significantly less than thickness width W1 providing decreased shielding of the magnetic field applied to the target region 210. As used here, a thin magnetic shield is considered a thickness in which an amount of magnetic field is felt on an exterior side of the shield through the shield and outside or away from the gap 140.

Figure 4B:
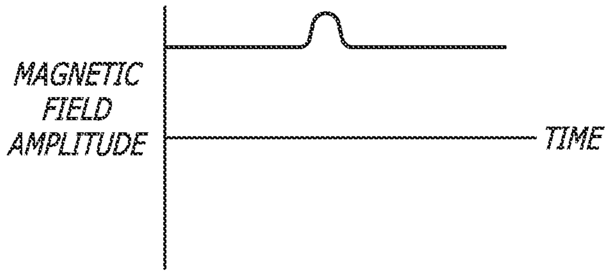
FIG. 4B shows a graph of an exemplary magnetic field according to an exemplary embodiment of the present disclosure as shown in FIG. 4A.

FIG. 4B shows a graph of magnetic field applied to the target region 210 over time according to the exemplary embodiment of the present disclosure as shown in FIG. 4A. In the graph, the x-axis is time and the y-axis shows magnetic field amplitude of the magnetic field applied to the target region 210 by the permanent magnet 120 in the configuration shown in FIG. 4A.

Here, the steady-state magnetic field amplitude is high and close in value as the non-shielded magnetic field amplitude. Thus, relative to the steady-state magnetic field, the non-shielded magnetic field pulse amplitude is low. In an exemplary embodiment, a thin magnetic shield is considered as being sufficient thin such that a magnetic field amplitude through the shielded portion of the magnetic shield is approximately half or more than the non-shielded magnetic field amplitude of the magnet.

Figure 5A:
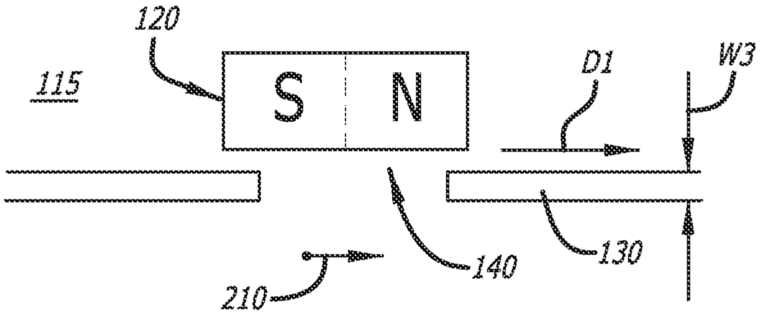
FIG. 5A is an exemplary partial representative component detail view of the magnetic stimulation device according to an exemplary embodiment of the present disclosure.

FIG. 5A shows a graph of an exemplary magnetic field applied to the target region 210 over time according to an exemplary embodiment of the present disclosure. This embodiment shares similar elements as those described above, as such their descriptions will be omitted and only differences will be described herein.

Here, the magnetic shield 130 moves in the direction D1 and is relatively thick with thickness width W3 of the magnetic shield 130 being significantly greater than the thickness width W2 and thickness width W1 providing increased shielding of the magnetic field applied to the target region 210. The thickness W3 may be sufficiently thick to shield approximately or more than 75%, 80%, 85%, 90%, 95%, 99% or more of the magnetic field amplitude.

Figure 5B:
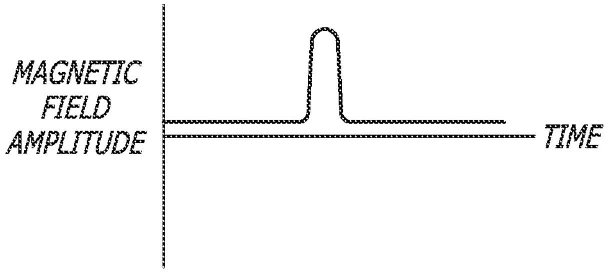
FIG. 5B shows an exemplary graph of a magnetic field according to an exemplary embodiment of the present disclosure as shown in FIG. 5A.

FIG. 5B shows a graph of magnetic field applied to the target region 210 over time according to the third embodiment of the present disclosure as shown in FIG. 5A. In the graph, the x-axis is time and the y-axis shows magnetic field amplitude of the magnetic field applied to the target region 210 by the permanent magnet 120 in the configuration shown in FIG. 5A.

Here, the steady-state magnetic field amplitude is nominal due to the shielding performance of the magnetic shield 130. Thus, relative to the steady-state magnetic field, the non-shielded magnetic field pulse amplitude is high. Moreover, in comparison to the embodiment shown in FIG. 4B, although the amplitudes are similar, the non-shielded magnetic field pulse amplitude is high relative to the steady-state magnetic field.

As such, moved in the direction D1 such that the non-shielded region 140 moves tangentially to the permanent magnet 120 and is situated between the permanent magnet 120 and target region 210, a unipolar changing magnetic field is created during the time the non-shielded region 140 allows the magnetic field generated by the permanent magnet 120 to penetrate the target region 210.

Figure 6A:
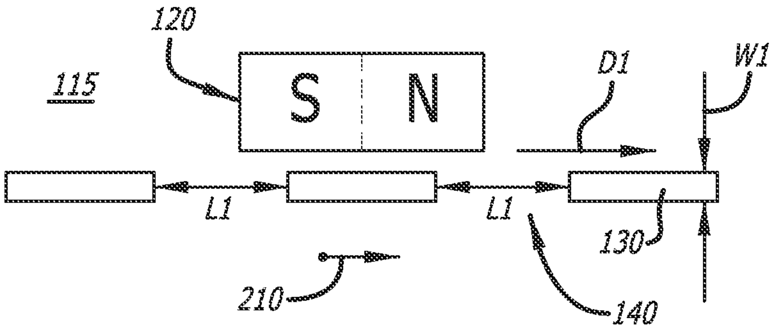
FIG. 6A is an exemplary partial representative component detail view of the magnetic stimulation device according to an exemplary embodiment of the present disclosure.

FIG. 6A is a representative partial component detail view of the magnetic stimulation system 100 according to an exemplary embodiment of the present disclosure. This embodiment shares similar elements as those described above, as such their descriptions will be omitted and only differences will be described herein.

Here, the permanent magnet 120 is positioned similarly as FIG. 2A with magnetic shield 130 moving in the direction D1. However, in this configuration, magnetic shield 130 includes a plurality of non-shielded regions 140 with each of the plurality of non-shielded regions 140 being of length L1. Exemplary embodiments may include a magnetic shield having a plurality of non-shielded regions.

The non-shielded regions may be of the same size, length, shape, or configuration, and/or may be of different sizes, lengths, shapes, or configurations. The shielded regions between the non-shielded regions may be of the same size, length, shape, or configuration, and/or may be of different sizes, lengths, shapes, or configurations. The combination of the shielded and non-shielded regions may be used to create a desired pattern of pulses including a desired pulse interval and/or pulse duration. The unshielded regions may be used to create pulses of different pulse duration and/or pulse interval.

Referring back to FIG. 6A, when the magnetic shield 130 is moved in the direction D1 and the plurality of non-shielded regions 140 move between the permanent magnet 120 and target region 210, a repetitive magnetic field stimulation is generated. For repetitive magnetic field stimulation, the duty cycle of shielded vs. non-shielded will affect the magnetic field amplitude over time.

Figure 6B:
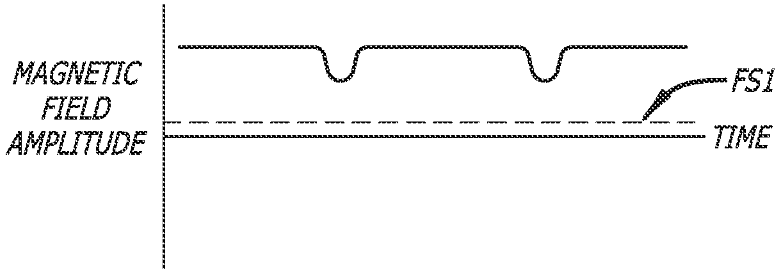
FIG. 6B shows an exemplary graph of magnetic field according to an exemplary embodiment of the present disclosure as shown in FIG. 6A.

FIG. 6B shows a graph of magnetic field applied to the target region 210 over time according to the exemplary embodiment of the present disclosure as shown in FIG. 6A. In the graph, the x-axis is time and the y-axis shows magnetic field amplitude of the magnetic field applied to the target region 210 by the permanent magnet 120 in the configuration shown in FIG. 6A.

In this embodiment, if the duty cycle allows only a short period of time non-shielded vs. a long period of time shielded (i.e., a short duty-cycle), a magnetic pulse will not affect the subsequent magnetic pulse. As the duty cycle increases in time (greater percentage of unshielded time), then the magnetic field amplitude may not drop down to a fully shielded value FS1 before beginning the next cycle. In this embodiment, the magnetic field pulse applied to target region 210 is shortened in duration due to the duty cycle of the moving magnetic shield 130. In yet another embodiment, similar results as shown in FIG. 6B can be achieved by decreasing the length L1 between the pluralities of non-shielded regions 140.

Figure 7:
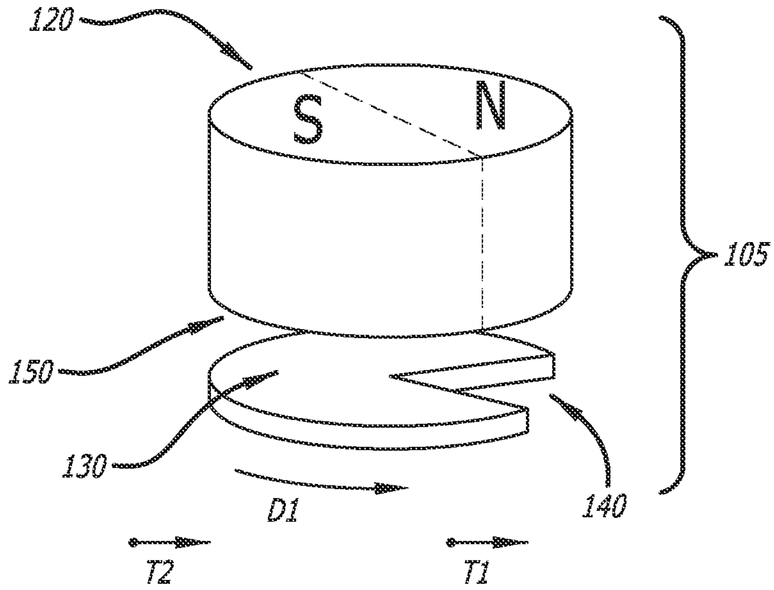
FIG. 7 illustrates an exemplary magnetic partial component view of an exemplary stimulation device with a disk-shaped magnetic shield according to an embodiment of the present disclosure.

FIG. 7 depicts an exemplary representative component view of an exemplary magnetic stimulation device 105 with disk-shaped magnetic shield 130 according to an embodiment of the present disclosure. This embodiment shares similar elements as those described above, as such their descriptions will be omitted and only differences will be described herein.

Here, the permanent magnet 120 is disk-shaped (or a cylinder rotated on its end) with the magnetic shield 130 rotating between the permanent magnet 120 and at least one target region via a wedge-shaped non-shielded region 140. This allows different target regions to be exposed to magnetic pulses at different phases of the magnetic shield 130 rotation.

For example, while target region T1 is exposed to the non-shielded magnetic field pulse, target region T2 is shielded by magnetic shield 130 and vice-versa during the rotation cycle of magnetic shield 130.

In an exemplary embodiment, the rest of the magnet, such as the portion of the magnet not potentially covered and/or exposed by the magnetic shield 130 having a non-shielded region, such as along lateral sides and/or a top surface away from a user, may be shielded.

Figure 8:
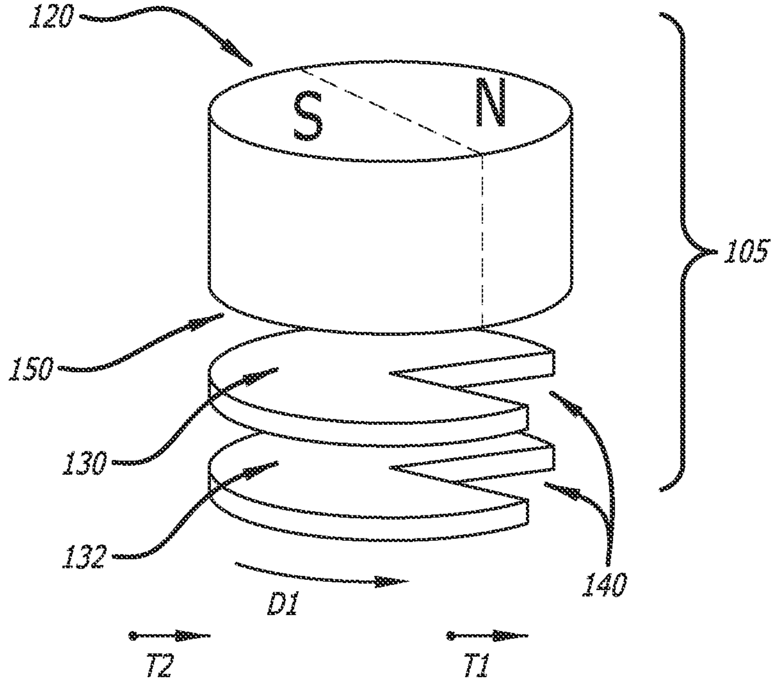
FIG. 8 depicts an exemplary magnetic partial component stimulation device with disk-shaped magnetic shield and stationary magnetic shield according to an exemplary embodiment of the present disclosure.

FIG. 8 depicts an exemplary representative component view of an exemplary magnetic stimulation device 105 with disk-shaped magnetic shield 130 and secondary magnetic shield 132 according to an embodiment of the present disclosure. This embodiment shares similar elements as those described above, as such, their descriptions will be omitted and only differences will be described herein.

Here, the permanent magnet 120 is disk-shaped (or a cylinder rotated on its end) with the magnetic shield 130 rotating between the permanent magnet 120 and the secondary magnetic shield 132. The secondary magnetic shield 132 can be, but is not limited to, stationary and is situated between magnetic shield 130 and a plurality of target regions. The secondary magnetic shield 132 can be rotated in the same direction and/or in an opposite direction to that of the first magnetic shield 130.

Moreover, the secondary magnetic shield 132 may include a wedge-shaped non-shielded region 140 similar to magnetic shield 130. This reduces different target regions being exposed to magnetic pulses at different phases due to the rotation cycle of the magnetic shield 130.

For example, while target region T1 is exposed to the non-shielded magnetic field pulse caused by the rotation cycle of magnetic shield 130, target region T2 is fully shielded by stationary secondary magnetic shield 132 throughout the entire rotation cycle.

Figure 9A:
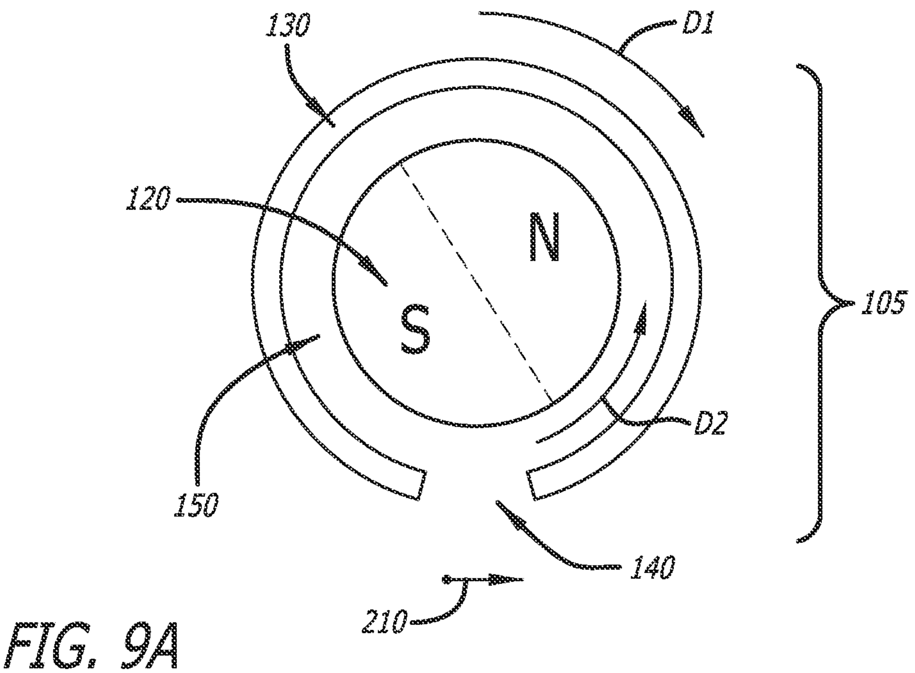
FIG. 9A depicts an exemplary partial component representative magnetic stimulation device with moveable permanent magnet and moveable magnetic shield according to an exemplary embodiment of the present disclosure.

FIG. 9A depicts a magnetic stimulation device 105 with moveable permanent magnet 120 and moveable magnetic shield 130 according to an exemplary embodiment of the present disclosure. This embodiment shares similar elements as those described above, as such their descriptions will be omitted and only differences will be described herein.

Here, the permanent magnet 120 is diametrically magnetized and is rotatable about its axis in a direction D2 and magnetic shield 130 is rotatable about the outer diameter of permanent magnet 120 in a direction D1 opposite the direction D2. Thus, it is possible to alter a magnetic field vector over time by synchronously moving the permanent magnet 120 with respect to the movement of the magnetic shield 130.

For example, when permanent magnet 120 is rotated at a speed that is ½ the rotation speed of magnetic shield 130, the magnetic field vector created will be in the opposite direction every other time the non-shielded region 140 exposes the target region 210 to the permanent magnet 120.

As before mentioned, the magnetic shield 130 may not completely shield the target region 210 from the permanent magnet 120. So, when the permanent magnet 120 rotates, the shielded magnetic field affecting the target region 210 may vary over time. Thus, a rotating diametrically magnetized cylindrical magnet may impart a sinusoidal magnetic field when shielded, with magnetic pulses being generated each time the non-shielded region 140 exposes the target region 210 to the permanent magnet 120.

Figure 9B:
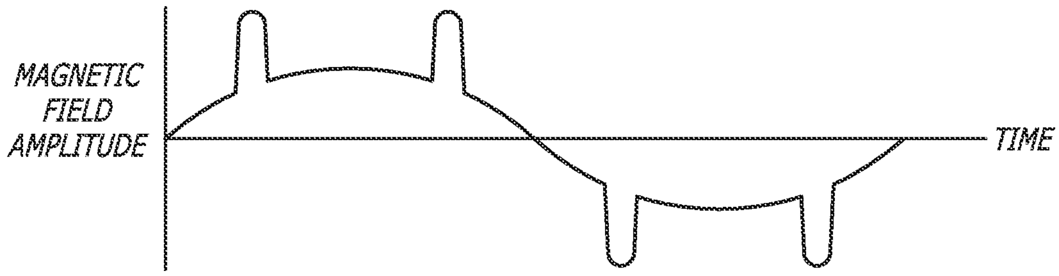
FIG. 9B shows an exemplary graph of an exemplary magnetic field according to the embodiment of the present disclosure as shown in FIG. 9A.

FIG. 9B shows a graph of an exemplary magnetic field applied to the target region 210 over time according to the embodiment of the present disclosure as shown in FIG. 9A. In the graph, the x-axis is time and the y-axis shows magnetic field amplitude of the magnetic field applied to the target region 210 by the permanent magnet 120 in the configuration shown in FIG. 9A.

The graph shows the configuration of a rotatable permanent magnet 120 synchronously moving with the rotating magnetic shield 130, and the resulting magnetic field magnitude sensed at the target region 210. As shown, the configuration allows a magnetic field with multiple frequency components to be applied to the target region 210. In this example, the magnetic stimulation applied to the target region 210 includes, but is not limited to, frequencies at the magnet rotation frequency as well as at the shield rotation frequency.

In an exemplary embodiment, the devices as described herein may comprise a support structure such as in the shape of a housing, helmet, head supported structure, head rest, arm, hand-device, wand, etc. The support structure may be configured to support the magnetic source, shielding, and other components described herein. In an exemplary embodiment, the shielding may be integrated into a housing and/or may be positioned within the housing. The shielding is configured to be positioned between the magnetic source and the patient, with the non-shielded region providing a gap there between in an area between the magnetic source and the patient. U.S. Pat. Nos. 9,713,729; and 9,962,555 are incorporated herein in their entirety. The disclosures in these patents provide exemplary components for the positioning of magnets, belts for rotating magnets, support structures, motors, etc. Exemplary embodiments described herein may include the same or similar features for supporting and moving magnets as described herein. Exemplary embodiments may incorporate shielding as described herein to provide the desired pulsed magnetic field. The components parts may be changed to support the rotation and/or translation of the magnet and/or shield as described herein. In an exemplary embodiment, a shield may be positioned adjacent to and/or around a portion of the magnet. In an exemplary embodiment, a shield may be positioned between the magnetic source and the patient, such as in a housing, integrated into the housing, and/or supported by the frame on an exterior side of the magnetic source.

Pursuant to these exemplary embodiments, a magnetic shield is moved in such a way that a permanent magnet is alternately exposed to or shielded from a target region creating a magnetic field applied to the target region. The applied magnetic field may be a pulsed magnetic energy, an alternating magnetic field, a varying magnetic field, or combinations thereof.

As used herein, the terms "about," "substantially," "relatively", "generally", "approximately", or other similar approximation for any numerical values, ranges, shapes, distances, relative relationships, etc. indicate a suitable dimensional tolerance that allows the part or collection of components to function for its intended purpose as described herein. Numerical ranges may also be provided herein. Unless otherwise indicated, each range is intended to include the endpoints, and any quantity within the provided range. Therefore, a range of 2-4, includes 2, 3, 4, and any subdivision between 2 and 4, such as 2.1, 2.01, and 2.001. The range also encompasses any combination of ranges, such that 2-4 includes 2-3 and 3-4.

Although embodiments of this invention have been fully described with reference to the accompanying drawings, it is to be noted that various changes and modifications will become apparent to those skilled in the art. Such changes and modifications are to be understood as being included within the scope of embodiments of this invention as defined by the appended claims. Specifically, exemplary components are described herein. Any combination of these components may be used in any combination. For example, any component, feature, step or part may be integrated, separated, sub-divided, removed, duplicated, added, or used in any combination and remain within the scope of the present disclosure. Embodiments are exemplary only, and provide an illustrative combination of features, but are not limited thereto.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

What is claimed is:

1. A magnetic stimulation apparatus comprising:

a permanent magnet configured to generate a magnetic field, the permanent magnet having a cylindrical shape;

a first magnetic shield configured to shield at least one target region from the magnetic field generated by the permanent magnet, the first magnetic shield having a circular shape and being aligned vertically with the permanent magnet in a manner that a vertical axis of the permanent magnet is coaxially aligned with a center the first magnetic shield; and a secondary magnetic shield configured to shield a plurality of target regions from the magnetic field generated by the permanent magnet, the secondary magnetic shield being positioned between the first magnetic shield and the at least one target region, the secondary magnetic shield including at least one gap region having a wedge-shape, wherein the first magnetic shield includes at least one gap region that is wedge-shaped and configured to expose the at least one target region to the magnetic field generated by the permanent magnet, wherein the first magnetic shield is positioned between one end of the permanent magnet and the secondary magnetic shield, and wherein the at least one gap region of the first magnetic shield is moveable and is configured to be coaxially vertically aligned with the at least one gap region of the secondary magnetic shield.

2. The magnetic stimulation apparatus according to claim 1, wherein the at least one target region is situated on or inside a user of the magnetic stimulation apparatus, and at least the at least one gap region of the first magnetic shield is moveable based on a predetermined speed.

3. The magnetic stimulation apparatus according to claim 1, wherein the permanent magnet is configured to be axially magnetized.

4. The magnetic stimulation apparatus according to claim 1, wherein the permanent magnet is configured to be diametrically magnetized.

5. The magnetic stimulation apparatus according to claim 4, wherein the first magnetic shield is positioned between one end of the permanent magnet and a plurality of target regions.

6. The magnetic stimulation apparatus according to claim 4, wherein the secondary magnetic shield is configured to be rotatable.

7. The magnetic stimulation apparatus according to claim 1, wherein the first magnetic shield includes a plurality of gap regions configured to expose the at least one target region to the magnetic field generated by the permanent magnet.

8. The magnetic stimulation apparatus according to claim 1, wherein the permanent magnet includes a north pole and a south pole, and wherein the north pole and the south pole are positioned to generate a polarity of the magnetic field in a direction tangential with respect to the at least one target region.

9. The magnetic stimulation apparatus according to claim 8, wherein the first magnetic shield is rotatable.

10. The magnetic stimulation apparatus according to claim 1, wherein the secondary magnetic shield is stationary.

11. A magnetic stimulation method comprising:

generating a magnetic field by a permanent magnet, the permanent magnet having a cylindrical shape;

shielding, by a first magnetic shield, at least one target region from the magnetic field generated by the permanent magnet, the first magnetic shield having a circular shape and being aligned vertically with the permanent magnet in a manner that a vertical axis of the permanent magnet is coaxially aligned with a center the first magnetic shield; and shielding, by a secondary magnetic shield, a plurality of target regions from the magnetic field generated by the permanent magnet, the secondary magnetic shield being positioned between the first magnetic shield and the at least one target region, the secondary magnetic shield including at least one gap region having a wedge-shape, wherein the first magnetic shield includes at least one gap region that is wedge-shaped and configured to expose the at least one target region to the magnetic field generated by the permanent magnet, wherein the first magnetic shield is positioned between one end of the permanent magnet and the secondary magnetic shield, and wherein the at least one gap region of the first magnetic shield is moveable based on a predetermined speed and is configured to be coaxially vertically aligned with the at least one gap region of the secondary magnetic shield.

12. The magnetic stimulation method according to claim 11, wherein the at least one target region is situated on a user.

13. The magnetic stimulation method according to claim 11, wherein the permanent magnet is configured to be axially magnetized.

14. The magnetic stimulation method according to claim 11, wherein the permanent magnet is configured to be diametrically magnetized.

15. The magnetic stimulation method according to claim 14, wherein the first magnetic shield is positioned between one end of the permanent magnet and a plurality of target regions.

16. The magnetic stimulation method according to claim 14, wherein the secondary magnetic shield is configured to be rotatable.

17. The magnetic stimulation method according to claim 16, wherein the secondary magnetic shield is stationary.

18. The magnetic stimulation method according to claim 11, wherein the first magnetic shield includes a plurality of gap regions configured to expose the at least one target region to the magnetic field generated by the permanent magnet.

19. The magnetic stimulation method according to claim 11, wherein the permanent magnet includes a north pole and a south pole, and wherein the north pole and the south pole are positioned to generate a polarity of the magnetic field in a direction tangential with respect to the at least one target region.

20. The magnetic stimulation method according to claim 19, wherein the first magnetic shield is rotatable.

* * * * *